(12) United States Patent
Wilson et al.

(10) Patent No.: US 7,264,775 B2
(45) Date of Patent: *Sep. 4, 2007

(54) IGNITER ASSEMBLY

(75) Inventors: Keith D. Wilson, Lees Summit, MO (US); Stephen B. Cummins, Kansas City, MO (US); Douglas C. Stewart, Mission, KS (US)

(73) Assignee: Midwest Research Institute, Inc., Kansas City, MO (US)

( * ) Notice: Subject to any disclaimer, the term of this patent is extended or adjusted under 35 U.S.C. 154(b) by 636 days.

This patent is subject to a terminal disclaimer.

(21) Appl. No.: 10/248,433

(22) Filed: Jan. 20, 2003

(65) Prior Publication Data

US 2004/0139876 A1  Jul. 22, 2004

(51) Int. Cl.
*G01N 31/00* (2006.01)

(52) U.S. Cl. .............................. 422/50; 422/51; 422/54

(58) Field of Classification Search .................. 422/50, 422/54, 83, 86, 91, 51
See application file for complete search history.

(56) References Cited

U.S. PATENT DOCUMENTS

| 2,904,406 | A | * | 9/1959 | Moore ......................... 436/139 |
|---|---|---|---|---|
| 3,437,880 | A | | 4/1969 | Profunser |
| 3,662,222 | A | | 5/1972 | Ray |
| 3,810,734 | A | | 5/1974 | Willson |
| 4,054,414 | A | | 10/1977 | Grob et al. |
| 4,176,903 | A | | 12/1979 | Cairo et al. |
| 4,271,453 | A | | 6/1981 | Yajaima et al. |
| 4,582,980 | A | | 4/1986 | Izzi |
| 5,153,673 | A | | 10/1992 | Amirav |
| 5,218,751 | A | | 6/1993 | Chen et al. .................... 29/621 |
| 5,741,711 | A | | 4/1998 | Amirav et al. |
| 6,922,238 | B2 | * | 7/2005 | Doynov et al. ............. 356/315 |

* cited by examiner

*Primary Examiner*—Jill Warden
*Assistant Examiner*—Samuel P. Siefke
(74) *Attorney, Agent, or Firm*—Blackwell Sanders LLP

(57) ABSTRACT

An igniter assembly for a pulsed flame photometric detector having a filament comprising a resistive heating wire between about 0.08 millimeter and about 0.40 millimeter in diameter wound into a coil having an inner diameter between about 0.40 millimeter and about 3.2 millimeters. The filament has an applied protective coating of an alloy of gold and palladium. The filament is detachably connected to a cable and connector assembly that connects the filament to a source of power in the pulsed flame photometric detector.

16 Claims, 1 Drawing Sheet

IGNITER ASSEMBLY

The U.S. Government has a paid-up license in this invention and the right in limited circumstances to require the patent owner to license others on reasonable terms as provided for by the terms of Contract No. DSWA01-98-D-0126 awarded by the Defense Threat Reduction Agency.

BACKGROUND OF INVENTION

The present invention relates to pulsed flame photometric detectors and the igniter assemblies associated therewith, and especially to portable detectors and the igniter assemblies associated therewith that are used in the field for onsite detection of trace amounts of chemical compositions. Such devices include a housing that contains and protects the detector and electrical power supply and an ionization chamber with one or more cables connecting the detector electronics and the ionization chamber to transmit power and electrical signals. One cable connects the electrical power supply to a filament located within the ionization chamber. The filament is heated by the passage of electrical current through the filament to ionize samples of chemical compositions that are injected into the ionization chamber. The ionized atoms of the chemical composition are detected and electrical signals indicative of the detected atoms are transmitted to the detector electronics to enable an operator to determine the composition of the injected chemical sample.

Operation of a pulsed flame photometric detector requires time for the detector to reach a steady state condition and for the ionization chamber, including the enclosed filament, to reach its operating temperature before a chemical sample can be injected into the ionization chamber for analysis.

A serious problem that limits effective use of portable pulsed flame photometric detectors is the power requirements necessary when utilizing standard filaments to achieve ionization. The use of a thicker wire as used in standard filaments has a great disadvantage of requiring more electrical power to ionize chemical samples. This requires a larger, heavier power supply, a disadvantage for a portable detector, and if the larger power supply is not selected, use of a smaller power supply shortens the time that the detector can be used. Use of thin wire filaments reduces the power requirements but it also reduces the lifecycle or longevity of the filament. A thin oxidation layer that forms on the filament during operation has provided some protection from degradation and from chemical attack, but this coating offers only limited protection for the filament.

Another problem is created by current designs in which the filament is attached to the end of a cable from the power supply. When the filament fails, the entire cable must be replaced. This requires that the device be completely opened up, giving the operator access to the detector body as well as the power supply so the filament and cable can be removed. For safety reasons, this may require some aspects of the instrument operation to be shut down. Following removal of the cable with the failed filament, a new cable with a new filament is installed. The pulsed flame photometric detector must then go through start-up and the time necessary to again reach steady state operating conditions. This is a severe problem when the detector is used in the field.

A pulsed flame photometer detector and methods for operating the detector are described in U.S. Pat. No. 5,153,673. The use of pulsed flame to combust or ionize a sample is described as is the use of detectors such as a thermionic ionization detector, an induced flourescence detector, an atomic absorption detector, an ion mobility spectrometer and a plasma emission detector for detecting the composition of the sample.

Coated filaments for other uses are also shown in the prior art such as the electric igniter construction shown in U.S. Pat. No. 3,810,734. However, in this patent, the coatings were selected for their ability to conduct electricity as well as their resistance to oxidation.

SUMMARY OF INVENTION

The present invention describes an igniter assembly for a pulsed flame photometric detector. More specifically the invention relates to an igniter assembly for portable pulsed flame photometric detectors that are used in the field for onsite detection of trace amounts of chemical compositions, especially chemical compositions containing sulfur or phosphorous compounds. The disadvantages of prior art detectors are overcome by the igniter assembly of the present invention that reduces the power consumption associated with achieving ionization of chemical samples by reducing the diameter of the filament. It also reduces the effects of chemical corrosion and improves the life span of the filament by providing a protective, corrosion resistant coating on the surface of the filament. Finally it provides a filament that is more easily and quickly replaced than in existing igniter designs. Maintenance and repair problems are also reduced by providing a filament that can be removed and replaced without requiring access to the detector electronics and power supply.

The present invention is also directed to a pulsed flame photometric detector that includes a housing containing a detector body enclosing an ionization chamber that is connected by a cable and connector assembly to the detector electronics. The ionization chamber contains a filament that is detachably connected to the cable and connector assembly. The cable and connector assembly conducts electrical power from a power supply in the detector electronics to the filament. The filament comprises a resistive heating wire wound into a coil and having a protective coating. The resistive wire is an alloy of nickel and chromium containing approximately 80 percent nickel and has a diameter between about 0.10 millimeter and about 0.32 millimeter. The coil has a diameter of about 0.80 millimeter. The protective coating is an alloy of gold and palladium having approximately 60 percent gold and is applied to the resistive wire as a coating between about 50 nanometers and about 100 nanometers thick. The filament is removable from the ionization chamber and detachable from the cable and connector assembly whereby the filament can be replaced without requiring access to the detector electronics and power supply.

The present invention is further embodied in an igniter assembly for a pulsed flame photometric device or other devices. The igniter assembly has a filament comprising a resistive heating wire produced from an alloy of nickel and chromium or an alloy of iron, chromium and aluminum. The resistive wire, a wire between about 0.08 millimeter and about 0.40 millimeter in diameter, is formed as a coil having an inner diameter between about 0.40 millimeter and about 3.2 millimeters. The preferred resistive heating wire, produced from an alloy of nickel and chromium, has a diameter of about 0.10 millimeter and is wound into a coil having an internal diameter of about 0.80 millimeter. The filament has a protective coating between about 10 nanometers and about 500 nanometers thick that is applied by a suitable method such as sputter coating. The protective coating material is chosen from among the noble metals, such as gold, palladium, platinum, rhenium, and rhodium, or alloys of them. A preferred coating material is an alloy of gold and palladium having between about 40 percent and about 80 percent gold. The filament is detachably connected to a cable and connector assembly that connects the filament to a source of power.

The objects and advantages of the present invention will become more apparent by reference to the following detailed description when viewed in light of the accompanying drawings.

DETAILED DESCRIPTION

Figure 1:
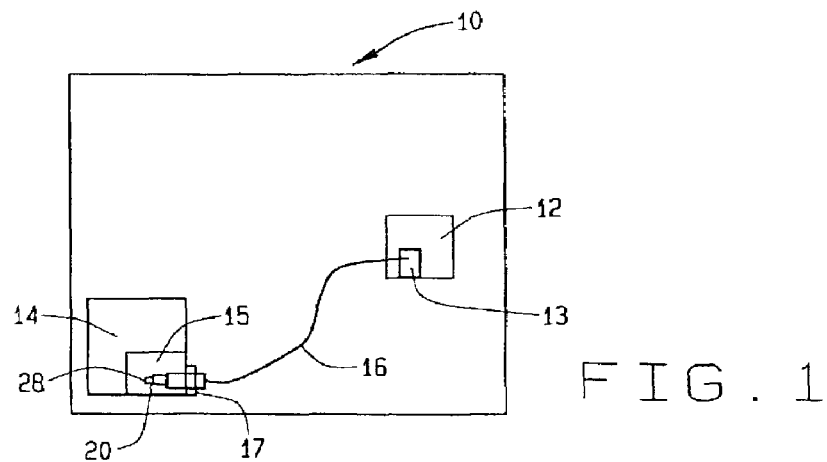
FIG. 1 is a block diagram of a pulsed flame photometric detector illustrating the apparatus of the present invention.

A block diagram of the pulsed flame photometric detector 10 of the present invention is shown in FIG. 1. The pulsed flame photometric detector 10 includes detector electronics 12, which includes a power supply 13, and detector body 14 which includes ionization chamber 115. Power supply 13 and ionization chamber 15 within detector body 14 are connected by cable and connector assembly 16. Igniter assembly 20, including filament 28, located within the ionization chamber 15 is detachably connected to the connector 17 on one end of cable and connector assembly 16. The cable and connector assembly 16 conducts electrical power from the power supply 13 within detector electronics 12 to igniter assembly 20 and filament 28.

Figure 2:
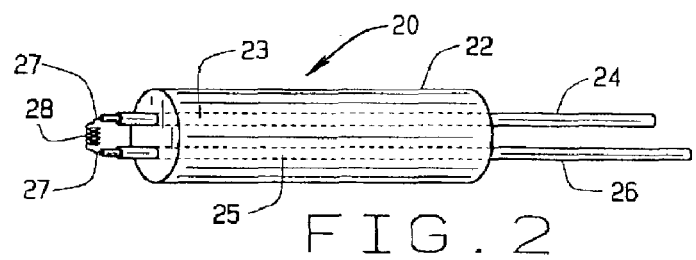
FIG. 2 is a perspective view of an igniter assembly constructed in accordance with the teachings of the present invention.
Figure 4:
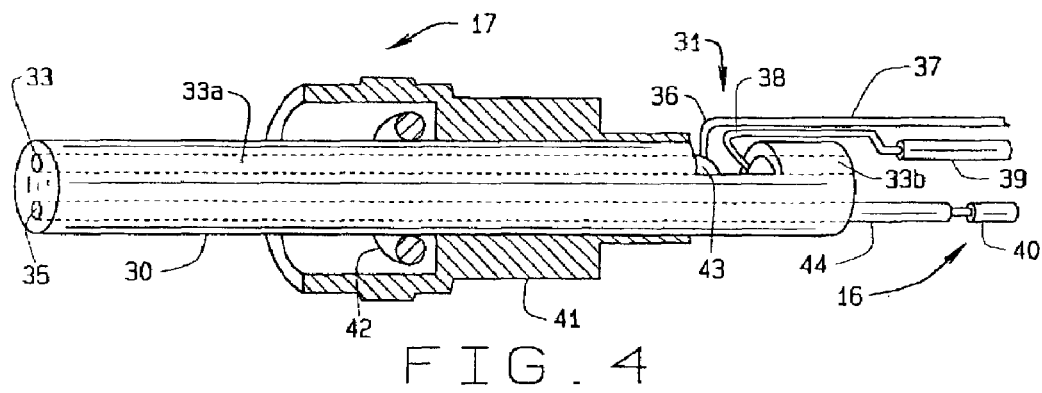
FIG. 4 is a partial section view of one end of the cable and connector assembly illustrating the connector for attachment of the igniter assembly in accordance with the teachings of the present invention.

Referring now to FIG. 2, a perspective view of igniter assembly 20 is shown. Igniter assembly 20 includes body 22 that has a cylindrical shape with holes 23, 25 radially separated from one another and passing longitudinally through body 22, that is, in a direction parallel the axis of cylindrical body 22. Tubes 24, 26 pass through holes 23, 25 and extend outwardly from body 22 in both directions parallel the axis. Filament 28 is attached to and suspended between one end of tubes 24, 26. The other ends of tubes 24, 26, the ends that extend from body 22 in a direction opposite filament 28, provide the electrical connection for igniter assembly 20 and filament 28 by detachable connection to connector 17 on one end of cable and connector assembly 16 as shown in FIGS. 1 and 4. These ends of tubes 24, 26 are of unequal length with tube 26 being about 1 millimeter to 2 millimeters longer than tube 24. The difference in length serves to make the connection to connector 17 easier.

Body 22 is a ceramic cylinder that is electrically non-conducting and capable of withstanding elevated temperatures of at least 350° C. present within the interior of ionization chamber 15 during operation of the pulse flame photometric device 10. For the purposes of this invention, body 22 can be fabricated from other electrically non-conducting materials that are capable of withstanding the operating temperature of the ionization chamber 15 such as quartz. Holes 23, 25 are radially spaced apart from one another and extend longitudinally through body 22, that is, the holes are spaced apart and pass completely through body 22 in a direction parallel the axis of the body 22. Tubes 24, 26 provide support and the electrical connection for filament 28. As such they must be capable of conducting electricity and of withstanding the elevated operating temperature of filament 28, approximately 1000° C. Tubes 24, 26 are constructed of stainless steel, although other metals capable of operation at the elevated temperatures within ionization chamber 15 may be used. Holes 23, 25 and tubes 24, 26 are sized to close tolerances to form a slip-fit as tubes 24, 26 must fit tightly within holes 23, 25 to prevent excessive leakage of air into the ionization chamber 15. To assure that holes 23, 25 are sealed against gas leaks, the ends of the holes may be sealed by a glass frit disk, ceramic paste or high temperature epoxy after tubes 24, 26 are inserted.

Filament 28 is attached to and suspended between one end of tubes 24, 26. The operating temperature of the filament is above the melting point of solder. Thus, the ends of filament 28 are spot welded to the ends of tubes 24, 26. Alternatively, for smaller diameter wire, such as wire having a diameter between about 0.08 millimeter and about 0.20 millimeter, the ends of filament 28 may be spot welded into small tubes 27 made of Inconel, stainless steel, or some other appropriate material and the tubes 27 are then spot welded into the ends of tubes 24, 26. Tubes 24, 26 extend longitudinally from body 22 so that filament 28 is positioned at least approximately 6.4 millimeters from the face of body 22. Filament 28 is formed from resistive heating wire that is wound into the shape of a coil. The wire is made from an alloy of nickel and chromium having from 40 percent to 90 percent, and preferably from 60 percent to 80 percent, nickel. A preferred resistive heating wire made from an alloy of nickel and chromium having 80 percent nickel is commercially available under the name Nichrome 80. The filament 28 is thin, having a diameter of from about 0.08 millimeter to about 0.40 millimeter, preferably having a diameter of from about 0.10 millimeter to about 0.32 millimeter and more preferably having a diameter of about 0.10 millimeter. Nichrome 80 wire with a diameter of 0.10 millimeter is commercially available. Wire of this diameter is fragile and is near the lower limit in order to maintain sufficient mechanical strength to withstand the stresses of installation of the filament, transportation of the device and heating and cooling of the filament during operation. To strengthen the filament and to provide better heating during operation, the wire is formed in the shape of a coil having an inner diameter of between about 0.40 millimeter and about 3.2 millimeters and preferably an inner diameter of about 0.80 millimeter. It is desirable to use a coil having a small diameter, but manufacturing the coil becomes more difficult as the diameter of the coil decreases.

To protect filament 28 from corrosive attack by the chemical samples and the vaporized gases a thin protective coating is bonded to the surface of the resistive heating wire. The protective coating ideally is resistant to or unaffected by high temperatures of up to 1000° C., has a high electrical resistivity so that it is substantially electrically non-conductive, has a thermal coefficient of expansion closely matching the thermal coefficient of expansion of the resistive heating wire forming the filament 28, is resistant to chemical attack in both oxidizing and reducing atmospheres and has a low oxygen permeability. Further, the material properties of the protective coating, in addition to the selection of the diameter and the composition of the resistive heating wire of the filament 28, must be optimized for compatibility with the goals of low power consumption and long life for filament 28. A protective coating providing the desired characteristics is provided by a coating of an alloy of gold and palladium having between 40 percent and 80 percent and preferably about 60 percent gold. The protective coating is applied to the filament by a suitable method such as the preferred sputter coating. Before applying the protective coating to filament 28, the body 22 that supports the filament 28 must be masked to prevent leakage current paths across the surface of body 22. Masking can be accomplished by brushing the ends of body 22, but not tubes 24, 26 or filament 28, with paint or lacquer and allowing body 22 to dry before proceeding with application of the protective coating. The protective coating is applied to filament 28 in a sputter-coating chamber using a gold/palladium target having the desired ratio of gold to palladium, such as the preferred ratio of 60 percent gold and 40 percent palladium. The power applied and the sputtering time are controlled to apply a protective coating having a thickness between 25 nanometers and 100 nanometers, and preferably between 50 nanometers and 100 nanometers to filament 28. The protective coating must be thick enough to provide corrosion protection for the filament but it must be thin enough to be substantially electrically non-conductive so that it does not interfere with heating of the filament by conducting an electric current. A gold/palladium protective coating less than 100 nanometers thick is thin enough to substantially not conduct electricity. Thus, such a coating offers corrosion protection for filament 28 while not affecting the flow of electrical current through the filament. Following application of the protective coating to filament 28, the masking material is removed from body 22 by agitation in an appropriate solvent bath. Other methods of application of the protective coating to filament 28 may be advantageously used. It is also recognized and anticipated that other materials including other metallic alloys, ceramics and some advanced plastics may be suitable as a protective coating for the filament providing the materials can achieve the above referenced desired characteristics. In particular, it is anticipated that several of the other noble metals such as platinum, rhenium and rhodium and their alloys, including alloys with gold or palladium, will be suitable for use as a protective coating for the filament.

Figure 3:
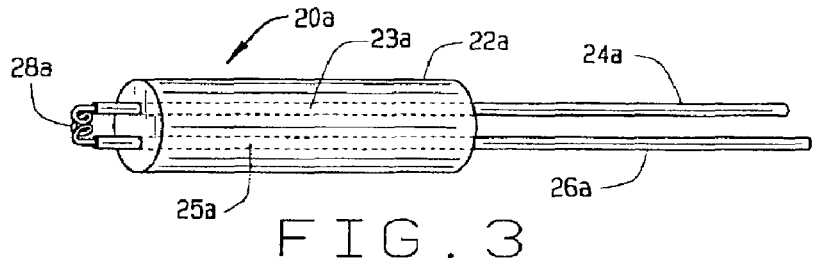
FIG. 3 is a perspective view of another embodiment of an igniter assembly constructed in accordance with the teachings of the present invention.

Referring now to FIG. 3, a perspective view of igniter assembly 20*a*, another embodiment of the present invention is shown. In FIG. 3 like numbers are used to illustrate features similar to those illustrated in the embodiment of the present invention shown in FIG. 2. Igniter assembly 20*a* includes body 22*a* that has a cylindrical shape with holes 23*a*, 25*a* radially separated from one another and passing longitudinally through body 22*a*, that is, in a direction parallel the axis of cylindrical body 22*a*. Tubes 24*a*, 26*a* pass through holes 23*a*, 25*a* and extend outwardly from body 22*a* in both directions parallel the axis. Filament 28*a* is attached to and suspended between one end of tubes 24*a*, 26*a*. The ends of filament 28*a* may be spot welded to the ends of tubes 24*a*, 26*a* or the ends of filament 28*a* may be inserted into the ends of tubes 24*a*, 26*a* before welding. The other ends of tubes 24*a*, 26*a*, the ends that extend from body 22*a* in a direction opposite filament 28*a*, provide the electrical connection for igniter assembly 20*a* and filament 28*a* by detachable connection to connector 17 on one end of cable and connector assembly 16 as shown in FIGS. 1 and 4. These ends of tubes 24*a*, 26*a* are of unequal length with tube 26*a* being from about 1 millimeter to 2 millimeters longer than tube 24*a*. The difference in length of tubes 24*a*, 26*a*, which is manifested in the direction opposite filament 28*a*, serves to make the connection to connector 17 easier. Further, tubes 24*a*, 26*a* are substantially longer, at least about 12 millimeters, than tubes 24, 26.

The elements of the embodiment of this invention illustrated as igniter assembly 20*a* in FIG. 3 and as igniter assembly 20 in FIG. 2 are substantially the same except filament 28*a* may differ from filament 28 in the diameter of the filament wire, in the composition of the filament wire and in the method for attaching the filament to its supporting tubes and tubes 24*a*, 26*a* are each at least approximately 12 millimeters longer than tubes 24, 26.

Filament 28*a* is a formed from resistive heating wire that is wound into the shape of a coil. The wire may be made from an alloy of iron, chromium and aluminum such as, for example, an alloy having from 4 percent to 5.5 percent aluminum, from 13 percent to 22 percent chromium and the balance iron. A preferred resistive heating wire made from such an alloy of iron, chromium and aluminum is commercially available under the name Kanthal D; however, other similar wire alloys may work equally well. Filament 28*a* is relatively thicker than filament 28, having a diameter of from about 0.15 millimeter to about 0.40 millimeter, preferably having a diameter of from about 0.20 millimeter to about 0.32 millimeter and more preferably having a diameter of about 0.32 millimeter. Kanthal D wire is more brittle than Nichrome 80 wire and it breaks more easily. Thus, it is desirable to use a thicker wire, such as a wire having a diameter of about 0.32 millimeter, when the Kanthal D wire is used as filament 28*a*. Since a thicker wire is used for filament 28*a*, the protective coating applied to the filament can be somewhat thicker than 100 nanometers without affecting the current flow through the filament.

In the embodiments above, the filament is formed from a resistive heating wire made from alloys of nickel and chrome and from alloys of iron, chromium and aluminum. While these are the preferred compositions for the wire used to make the filament, it is expected that other resistive heating wires would also be suitable for use as the filament in a pulse flame photometric detector.

FIG. 4 is a partial section view of one end of the cable and connector assembly 16 illustrating the connector 17 for attachment of the igniter assembly in accordance the teachings of the present invention. Connector 17 includes base 30, a ceramic cylinder that is electrically non-conducting and capable of withstanding elevated temperatures of at least 250° C. For the purposes of this invention, base 30 can be fabricated from other electrically non-conducting materials that are capable of withstanding the operating temperature such as Vespel® or other high temperature plastics. Base 30 has a cylindrical shape with holes 33, 35 radially separated from one another and passing longitudinally through base 30, that is, in a direction parallel the axis of cylindrical base 30. Hollow metallic tubes 43, 44 are located within holes 33, 35 and extend from one end to provide electrical connection points for cable 16. Base 30 has the same diameter as body 22, shown in FIG. 2, and the inner diameter of metallic tubes 43, 44 within holes 33, 35 in base 30 are located and sized to match holes 23, 25 in body 22. Base 30 also has notch 31 removing a portion of hole 33 and tube 43. Notch 31 is sized to separate hole 33 into two portions, hole portion 33*a* and hole portion 33*b*, having a discontinuity therebetween without interference with the continuity of hole 35. Notch 31 is sized longitudinally to provide sufficient space for electrical connector 36 to be attached to tube 43, where it protrudes about 1.5 millimeter from hole portion 33a, and for electrical connector 38 to be situated to provide connection to tube 24a or 26a when igniter assembly 20a is fully inserted, before tube 24a or 26a enters hole portion 33b. Wires 37, 39 are connected to electrical connectors 36 and 38 respectively. Electrical connector 38 is further situated so it does not provide connection to tube 24 or 26 when igniter assembly 20 is fully inserted, that is the shorter tubes 24, 26 of igniter assembly 20 are sized such that they reach electrical connector 36, but are not sufficiently long to extend across notch 31 to make electrical contact with electrical connector 38. Wire 40 is electrically connected to tube 44, which extends through hole 35. Wires 37, 39 and 40 are wrapped together, not shown, to form the cable portion of cable and connector assembly 16 providing the electrical connection between connector 17 and detector electronics 12 as shown in FIG. 1. Connector 17 further includes connector cap 41 to provide a screw connection to attach connector 17 to detector body 14. While a screw connection is shown, other methods for connecting the cable and connection assembly 16 to detector body 14 are equally acceptable. Connector cap 41 includes o-ring 42 to provide a seal against air entering ionization chamber 15 around the circumference of base 30. When attached using connector cap 41, connector 17 extends into the interior of ionization chamber 15 to position igniter assembly 20 properly for operation.

During operation of the pulsed flame photometric detector 10, igniter assembly 20 or 20a is detachably attached to connector 17. For portable pulsed flame photometric detectors the size of the filament and the size and capacity of the power supply are often determinative of the usefulness of the detector. If the filament is large enough to have a greater resistance to damage when the device is transported, then the filament requires more electrical power for heating to ionize the chemical samples. If the filament is smaller to reduce its power consumption, then the filament is fragile and more easily broken. Similarly, the power supply must be sized to provide sufficient power to make the pulsed flame photometric detector useful. If a larger filament is used without increasing the capacity of the power supply, the operating life of the detector is shortened. However, the larger the power supply, the more it weighs and the less portable the detector becomes.

Filaments 28, 28a differ primarily in the preferred size of the wire used to make the filament, and also in the preferred composition of the wire and the preferred method for attaching the filament to its supporting tubes. As discussed above with respect to FIG. 2, filament 28 is formed from resistive heating wire made from an alloy of nickel and chromium having a preferred diameter of about 0.10 millimeter. As discussed above with respect to FIG. 3, filament 28a is formed from a resistive heating wire made from an alloy of iron, chromium and aluminum having a preferred diameter of about 0.32 millimeter. The iron/chromium/aluminum wire is more brittle than the nickel/chrome wire and it breaks more easily. Thus, it is not as appropriate for use in the thinner filament 28.

The different filaments, 28, 28a, have different electrical power requirements and the pulsed flame photometric detector 10 must distinguish between the filaments to enable proper operation of the detector. Electrical connector 38 mounted in notch 31 in base 30 is used to allow the detector electronics 12 to distinguish between filaments 28, 28a.

To connect igniter assembly 20 to connector 17, tubes 24, 26 extending from body 22 are inserted into tubes 43, 44 in base 30. Tubes 43, 44, like holes 23, 25 in body 22, are sized to close tolerances to form a tight slip-fit with tubes 24, 26. To disconnect igniter assembly 20 from connector 17, tubes 24, 26 are removed from tubes 43, 44. This type connection is preferred for its ease of use, however, other methods for detachably connecting the igniter assembly 20 to base 30 may be equally suitable. Tubes 24, 26 do not have sufficient length to extend through base 30 to make electrical contact with electrical connector 38. They do, however, make electrical contact with tubes 43, 44 to complete the electrical circuit between filament 28 and power supply 13. A circuit, not shown, within power supply 13 or detector electronics 12 identifies filament 28 by the absence of electrical contact between tube 43 and electrical connector 38 and the appropriate electrical current is provided to filament 28 for proper operation of the pulsed flame photometric detector 10.

The connection of igniter assembly 20a to connector 17 is similar to the connection of igniter assembly 20. Tubes 24a, 26a extending from body 22a are inserted into tubes 43, 44 in base 30. Tubes 43, 44, like holes 23a, 25a in body 22a, are sized to close tolerances to form a tight slip-fit with tubes 24a, 26a. Tubes 24a, 26a are each about 12 millimeters longer than tubes 24, 26. Tubes 24a, 26a have sufficient length to extend through base 30, and across notch 31, to make electrical contact with connector 38, as well as tubes 43, 44 to complete the electrical circuit between filament 28a and power supply 13. A circuit, not shown, within power supply 13 or detector electronics 12 identifies filament 28a by the electrical contact between tube 43 and electrical connector 38 and the appropriate electrical current is provided to filament 28a for proper operation of the pulsed flame photometric detector 10. In view of the differences between the filaments 28, 28a, the appropriate electrical current provided to filament 28a is also different from that provided to filament 28.

Filaments 28, 28a can be replaced easily by removing connector cap 41 from detector body 14. Removal of connector cap 41 allows connector 17 and igniter assembly 20, 20a to be removed from ionization chamber 15. Igniter assembly 20 with filament 28, or igniter assembly 20a with filament 28a, can be detached from connector 17, by removing tubes 24, 26, or tubes 24a, 26a, from tubes 43, 44, and replaced without disconnecting the cable and connector assembly 16 from power supply 13. Thus, filaments 28, 28a can be replaced without requiring access to power supply 13. This easy replacement of the filament reduces the time required to replace a filament. It also reduces maintenance and repair problems by providing a filament that can be removed and replaced without access to the more sensitive areas of the device.

Although the present invention has hereinabove been described with respect to the illustrated embodiments, it will be understood that the invention is capable of modification and variation without departing from the scope of the invention and the invention is limited only by the following claims.

The invention claimed is:

1. An igniter assembly for a pulsed flame photometric detector comprising:
   a. a filament comprising a non-catalytic resistive heating wire,
   b. said fliament having an applied protective coating which is thin enough to be substantially electrically non-conductive but yet thick enough to provide corrosion protection from chemical attacks, said protective coating comprising an alloy of gold and palladium having between 40 and 80 percent gold and being between about 10 nanometers and about 500 nanometers thick, said protective coating having a thermal coefficient of expansion closely matching the thermal coefficient of expansion of said resistive heating wire, c. said filament being detachably connected to a cable and connector assembly, and d. said cable and connector assembly connecting said filament to a source of power.

2. The igniter assembly of claim 1 wherein said resistive heating wire is selected from the group consisting of an alloy of nickel and chromium having between 40 percent and 90 percent nickel and an alloy of iron, aluminum and chromium.

3. The igniter assembly of claim 1 wherein said resistive heating wire is between about 0.08 millimeter and about 0.40 millimeter in diameter.

4. The igniter assembly of claim 2 wherein said resistive heating wire is an alloy of iron, chromium and aluminum.

5. The igniter assembly of claim 1 wherein said filament comprises a resistive beating wire formed in a coil having an inner diameter between about 0.40 millimeter and about 3.2 millimeters.

6. The igniter assembly of claim 2 further comprising means for identifying the resistive heating wire selected and for providing an appropriate current to said resistive heating wire based upon that identification.

7. The igniter assembly of claim 6 wherein said means includes a pair of tubes each having one end portion thereof attached to said resistive heating wire and each having the opposite end portion thereof extending in a direction away from and opposite said resistive heating wire, the pair of tubes associated with the resistive heating wire formed of an alloy of nickel and chromium having their respective opposite end portions of a different length as compared to the length of the respective opposite end portions of the pair of tubes associated with the resistive heating wire formed of an alloy of iron, aluminum and chromium.

8. The igniter assembly of claim 7 wherein said means further includes an electrical connector associated with said cable and connector assembly, said electrical connector having at least one electrical connection point which will make with electrical contact with one of the pair of tubes associated with either a resistive heating wire formed of an alloy of nickel and chromium or a resistive heating wire formed of an alloy of iron, aluminum and chromium but not both.

9. An igniter assembly for a pulsed flame photometric detector comprising:

a. a filament comprising a non-catalytic resistive heating wire between 0.08 millimeter and about 0.40 millimeter in diameter wound into a coil having an inner diameter between about 0.40 millimeter and 3.2 millimeters, b. said filament having an applied protective coating comprising an alloy of gold and palladium having between 40 percent and 80 percent gold, said protective coating being between about 25 nanometers and about 100 nanometers thick and being substantially electrically non-conductive and having a thermal coefficient of expansion closely matching the thermal coefficient of expansion of said resistive heating wire, c. said filament being detachably connected to a cable and connector assembly, and d. said cable and connector assembly connecting said filament to a source of power in said pulsed flame photometric device.

10. The igniter assembly of claim 9 wherein said resistive heating wire is selected from the group consisting of an alloy of nickel and chromium having between 40 percent and 90 percent nickel and an alloy of iron, chromium and aluminum.

11. The igniter assembly of claim 10 further comprising means for identifying the resistive heating wire selected and for providing an appropriate current to said resistive heating wire based upon that identification.

12. The igniter assembly of claim 10 wherein said resistive heating wire is an alloy of nickel and chromium having between 40 percent and 90 percent nickel.

13. The igniter assembly of claim 12 wherein said resistive heating wire is between about 0.10 millimeter and about 0.32 millimeter in diameter.

14. The igniter assembly of claim 10 wherein said resistive heating wire is an alloy of iron, chromium and aluminum.

15. An igniter assembly comprising:

a. a filament comprising a non-catalytic resistive heating wire wound into a coil and having a protective coating applied thereto, 1) said resistive heating wire comprising an alloy of nickel and chromium and having a diameter between about 0.08 millimeter and about 0.40 millimeter, 2) said coil having an inner diameter between about 0.40 millimeter and about 3.2 millimeters, and 3) said protective coating comprising an alloy of gold and palladium, having a thermal coefficient of expansion closely matching the thermal coefficient of expansion of said resistive heating wire and having a thickness between about 10 nanometers and about 100 nanometers, b. said filament being detachably connected to a source of electrical power.

16. An igniter assembly for use in a pulsed flame photometric detector comprising:

a. a filament comprising a non-catalytic resistive heating wire having a thin protective coating applied thereto to protect against premature failure due to corrosion and chemical attack on said resistive heating wire, 1) said resistive heating wire being selected from the group consisting of an alloy of nickel and chromium having between 40 percent and 90 percent nickel and an alloy of iron, chromium and aluminum, 2) said protective coating comprising an alloy of gold and palladium, b. said filament being detachably connected to a source of electrical power, and c. means for identifying the resistive heating wire selected from the group and for providing a different appropriate current to each of said resistive heating wires based upon that identification, said means including a pair of tubes extending beyond both opposed end portions of said igniter assembly and an electrical connector, one end portion of said pair of tubes being attached to said resistive heating wire, the opposite end portions of said pair of tubes associated with the resistive heating wire formed of an alloy of nickel and chromium being of a different length than the opposite end portions of said pair of tubes associated with the resistive heating wire formed of an alloy of iron, aluminum and chromium, d. said electrical connector having a plurality of electrical connection points for making electrical contact with said pair of tubes, a first combination of said plurality of electrical connection points making electrical contact with a resistive heating wire formed of an alloy of nickel and chromium and a second combination of said plurality of electrical connection points making electrical contact with a resistive heating wire formed of an alloy of iron, aluminum and chromium, the resistive heating wire selected being identified based upon said first and second combination of electrical connection points making electrical contact with said pair of tubes.

* * * * *

UNITED STATES PATENT AND TRADEMARK OFFICE
CERTIFICATE OF CORRECTION

| | | |
|---|---|---|
| PATENT NO. | : 7,264,775 B2 | Page 1 of 1 |
| APPLICATION NO. | : 10/248433 | |
| DATED | : September 4, 2007 | |
| INVENTOR(S) | : Keith D. Wilson | |

It is certified that error appears in the above-identified patent and that said Letters Patent is hereby corrected as shown below:

Claim 1, Col. 8, line 62, delete "fliament" and replace with -- filament --

Claim 5, Col. 9, line 20, delete "beating" and insert -- heating --

Claim 8, Col. 9, line 42, prior to the word "electrical" delete "with"

Claim 9, Col. 9, line 50, prior to the number "0.08" insert -- about --

Signed and Sealed this

Twentieth Day of November, 2007

JON W. DUDAS
*Director of the United States Patent and Trademark Office*